United States Patent [19]

Century

[11] Patent Number: 5,570,686
[45] Date of Patent: Nov. 5, 1996

[54] POWDER DISPENSER

[76] Inventor: Theodore J. Century, 702 W. Carpenter La., Philadelphia, Pa. 19119

[21] Appl. No.: 551,711

[22] Filed: Nov. 1, 1995

Related U.S. Application Data

[62] Division of Ser. No. 401,079, Mar. 8, 1995, Pat. No. 5,513,630.

[51] Int. Cl.$^6$ .............................. A61M 15/00; A61M 3/00; B05B 11/02
[52] U.S. Cl. ................ 128/203.12; 128/203.15; 222/631; 604/218; 604/241; 604/243
[58] Field of Search ........................ 128/200.14, 200.21, 128/200.22, 203.12, 203.15, 203.23, 203.28; 604/181, 218, 236, 240, 243, 275, 278, 241; 137/268, 846, 847, 855; 222/631, 633

[56] References Cited

U.S. PATENT DOCUMENTS

| | | | |
|---|---|---|---|
| 280,202 | 6/1883 | Mattson | 128/203.13 |
| 2,722,935 | 11/1955 | Thompson et al. | 128/203.15 |
| 3,422,844 | 1/1969 | Grise | 137/847 |
| 4,306,554 | 12/1981 | Schwartz et al. | 604/236 |
| 4,344,573 | 8/1982 | De Felice | 239/320 |
| 4,524,805 | 6/1985 | Hoffman | 137/846 |
| 4,620,847 | 11/1986 | Shishov et al. | 604/58 |
| 5,010,925 | 4/1991 | Atkinson et al. | 137/847 |
| 5,063,025 | 11/1991 | Ito | 422/100 |
| 5,161,524 | 11/1992 | Evans | 128/203.15 |

FOREIGN PATENT DOCUMENTS

| | | |
|---|---|---|
| 0435063 | 7/1991 | European Pat. Off. . |
| 1591990 | 9/1990 | U.S.S.R. . |
| 92/06727 | 4/1992 | WIPO . |
| WO94/07514 | 7/1992 | WIPO . |
| WO93/00951 | 9/1993 | WIPO . |

OTHER PUBLICATIONS

Vernay Duckbill Check Valves Brochure, Vernay Laboratories, Inc., Yellow Springs, Ohio 45387–0310 (1992) 4 Pages.

*Primary Examiner*—V. Millin
*Assistant Examiner*—Eric P. Raciti
*Attorney, Agent, or Firm*—Paul & Paul

[57] ABSTRACT

A dispenser provides pulmonary delivery of a powder dose to a subject. The dispenser is adapted to be brought into connection with an actuator which introduces an amount of a gas for dispensing the powder dose. The dispenser includes a chamber for receiving the powder dose and a valve for permitting passage of the powder dose only when the actuator introduces the gas into the dispenser. The powder dose is passed from the dispenser for pulmonary delivery to the subject.

14 Claims, 7 Drawing Sheets

| TRIAL NO. | POWDER DOSE SIZE (mg) | PERCENT OF DOSE REMAINING AFTER SINGLE ACTUATION | ACTUATING AIR VOLUME (cc) |
|---|---|---|---|
| 1 | 2.7 | 5 | 3 |
| 2 | 3.1 | 7 | 3 |
| 3 | 2.1 | 2.5 | 3 |
| 4 | 2.2 | 7.5 | 3 |
| 5 | 2.7 | 2 | 1 |
| 6 | 13.5 | 2.5 | 3 |

EFFICIENCY OF DRY POWDER DISPENSER, EXPRESSED AS PERCENT OF INITIAL POWDER DOSE REMAINING IN DEVICE AFTER A SINGLE ACTUATION.

Figure 14:
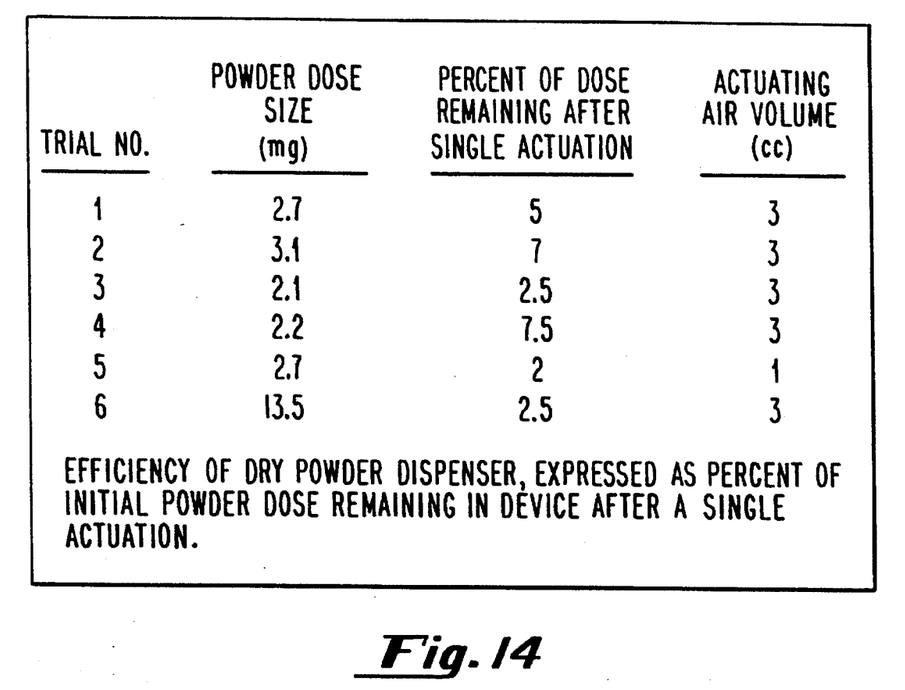

*Fig. 14*

| TRIAL NO. | POWDER DOSE SIZE (mg) | PERCENT OF DOSE REMAINING AFTER SINGLE ACTUATION | ACTUATING AIR VOLUME (cc) |
|---|---|---|---|
| 1 | 5.25 | 7 | 3 |
| 2 | 5.05 | 2.5 | 3 |

EFFICIENCY OF DRY POWDER DISPENSER IN CONJUNCTION WITH 18-INCH LONG TUBE, EXPRESSED AS PERCENT OF INITIAL POWDER DOSE REMAINING IN DEVICE AFTER A SINGLE ACTUATION.

Figure 15:
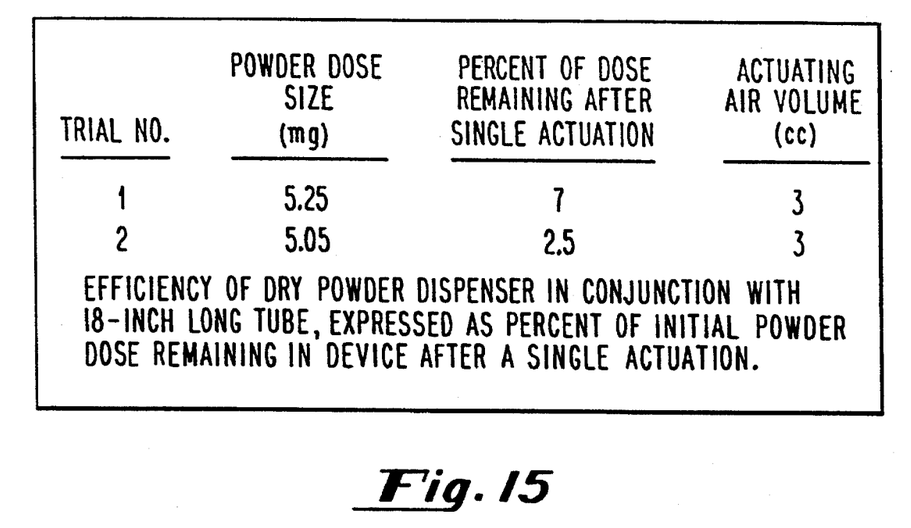

*Fig. 15*

POWDER DISPENSER

CROSS-REFERENCE TO RELATED APPLICATIONS

This Application is a division of U.S. patent application Ser. No. 08/401,079 filed Mar. 8, 1995, now U.S. Pat. No. 5,513,630 issued May 7, 1996.

BACKGROUND OF THE INVENTION

1. Field of the Invention

The present invention relates generally to powder dispensers and more particularly to the pulmonary route of drug administration.

2. Description of the Prior Art

The lungs present an attractive alternative to parenteral and oral routes for the administration of drugs for the treatment of systemic as well as pulmonary disorders. This is due to the large surface area and extensive vascularization of the lung, as well as to the high permeability of the airway and alveolar epithelia.

Much of the current interest in the pulmonary route of drug delivery has centered on the development of methods which use jet nebulizers or MDI's (multiple dose inhalers) for the administration of aerosols of solutions of a variety of drug substances such as antibiotics, bronchodilators, anti-inflammatory steroids, antiproteases, polypeptides, surfactant and gene transfer products. However, while this approach offers relative freedom from a number of systemic side-effects when compared with parenteral or oral methods, the efficiency of delivery is typically low (1–20%), and there are undesirable local side-effects such as cough, airway irritation and bronchoconstriction. Furthermore, substances which are not water-soluble are generally not amenable to this approach. Finally, the chlorofluorocarbons which are typically used as propellants in MDI's are currently being phased out for environmental reasons.

For these reasons, attention has recently shifted to the possibility of using inhaled dry powders as a way of accessing the pulmonary route of drug administration. These studies almost invariably involve a device in which a small, precisely-metered amount of powder is presented to an airstream generated by the patient's inhalation, although additional sources of energy (mechanical disruption, compressed air) are occasionally used to improve powder dispersion. Due to the inherent variability in a number of factors, including oropharyngeal geometry, force of inhalation, powder formulation, and the fraction of the powder "dose" actually presented to the airstream in the device, the delivery of a precise amount of a dry powder to the lower respiratory tract by inhalation is highly problematic. For example, in human trials of prior art dry powder inhalers, only 5–14% of the available powder dose actually reached the lungs. Furthermore, while these types of inhalers may be appropriate for prophylactic administration of drugs such as insulin or parathyroid hormone, patients with asthma or other forms of acute bronchoconstriction are unable to generate enough airflow to activate these devices. This is especially true of children and infants.

In view of the foregoing, it is apparent that there is a strong need for both improved pulmonary delivery for drug administration and also in dispensers which can be adapted for this purpose.

SUMMARY OF THE INVENTION

The present invention provides an apparatus for pulmonary delivery of a powder dose to a subject. For this purpose, the present invention provides means for receiving the powder dose, means for actuating the apparatus for delivery of the powder dose and means for discharging the powder dose for pulmonary delivery to the patient. A valve means is also provided for permitting passage of the powder dose in a first direction upon actuation of the apparatus and for preventing passage of the powder dose in the first direction when the apparatus is not actuated.

The present invention also discloses a method for dispensing an amount of a powder dose from a powder dispenser wherein substantially the entire powder dose is dispensed from the powder dispenser. The powder dispenser includes a dispenser assembly which is adapted for connection with an actuating means for dispensing of the powder dose. The dispenser assembly includes a passage therethrough for delivery of the powder dose and the passage of the dispenser assembly is configured for delivery of substantially the entire amount of the powder dose. In accordance with this aspect of the present invention, a method is disclosed which includes the steps of providing the powder dose in the dispenser assembly, providing the dispenser assembly in communication with the actuating means and actuating the actuating means for dispensing substantially the entire amount of the powder dose from the dispenser.

In another aspect of the present invention, a flow regulating valve is provided which permits passage of matter in a first direction of the valve and prevents passage of matter in a second direction of the valve which is opposite of the first direction. For this purpose, the flow regulating valve comprises a generally elongated first body member and a pair of substantially parallel lips extending from the first body member. The lips include a passage which extends therebetween and through the first body member. A second generally elongated body member is also provided and the lips which extend from the first body member are also connected to the second body member with the passage through the lips also extending through the second body member.

In accordance with the flow regulating valve set forth above, a method according to the present invention is also provided which includes the steps of providing first and second valve members and each valve member includes as portions thereof a generally elongated body member and a pair of substantially parallel lips. The method further includes the steps of substantially removing the lips of the second valve member and inserting the lips of the first valve member into a passage extending through the second valve member.

Another aspect of the present invention is to provide an apparatus for providing dispersion of a powder dose for delivery. For this purpose, the apparatus comprises means for receiving the powder dose and means for dispensing the powder dose from the apparatus. Also provided is means for actuating the apparatus including introducing an amount of a gas into the apparatus for delivery of the powder dose. Means for regulating the introduction of the gas into the apparatus is also provided. Further, valve means is also provided which permits passage of the powder dose upon actuation of the apparatus and prevents passage of the powder dose when the apparatus is not actuated. The structure of the valve means includes a generally elongated first body member and a pair of substantially parallel lips extending therefrom.

In accordance with the present invention, an object is provide an improved apparatus and method for the pulmonary delivery of a powder dose to a subject.

Figure 4A:
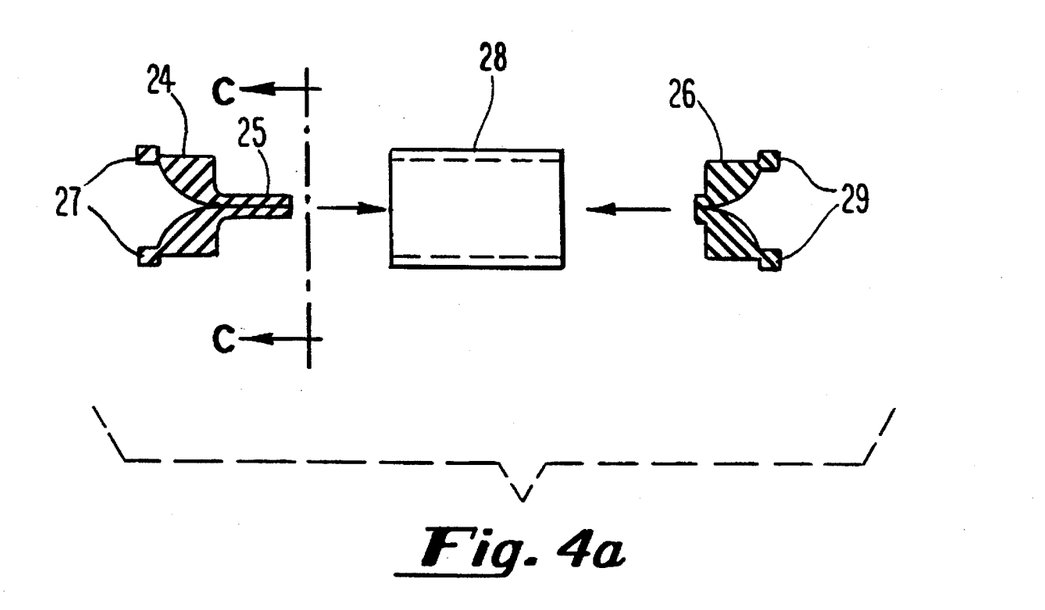

Another object of the present invention is to provide a powder dispenser adapted for use as a pulmonary delivery device wherein substantially the entire powder dose loaded into the dispenser is dispensed therefrom.

Still another object of the present invention is to provide an improved apparatus which provides dispersion of a powder dose for delivery.

Still a further object of the present invention is to provide an improved valve which can be utilized in a dispenser device which is adapted for permitting passage of matter in a first direction through the valve and prevents passage of matter in a second direction opposite the first direction.

Still another object of the present invention is to provide a powder dispenser which is sufficiently simple in design and operation. These and other objects of the present invention will become more readily apparent when taken into consideration with the following description and the attached drawings.

BRIEF DESCRIPTION OF THE DRAWINGS

FIG. 1 is an elevational view illustrating a powder dispenser according to a preferred embodiment of the present invention;

FIG. 2 is a sectional side elevational view of the powder dispenser of FIG. 1;

FIG. 3 is an exploded sectional elevational view of the powder dispenser of FIG. 1;

FIG. 4*a* is an exploded sectional elevational view illustrating a flow regulating valve of FIG. 1;

FIG. 4*b* is a front elevational view of the flow regulating valve of FIG. 1;

FIG. 5 is a front elevational view of an air guide of FIG. 1;

FIG. 6 is a sectional side elevational view illustrating a second embodiment of the powder dispenser according to the present invention;

FIG. 7 is an elevational view illustrating a third embodiment of the powder according to the present invention;

FIG. 8 is a sectional side elevational view of the powder dispenser of FIG. 7;

FIG. 9 is an exploded view of the powder dispenser of FIG. 8;

FIG. 10 is a front elevational view illustrating a guide member of FIG. 7;

FIG. 11 is a perspective view illustrating an apparatus for loading a powder dose into a powder dispenser of the present invention, the apparatus being shown applied to the powder dispenser according to the second embodiment of the present invention for illustration purposes;

FIGS. 12*a* and 12*b* are elevational views illustrating an apparatus for charging a syringe with gas for use with the powder dispenser according to the present invention;

FIG. 13 illustrates a sectional elevational view of an aerodynamic guide for use with the powder dispenser according to the present invention, the aerodynamic guide being shown with a powder dispenser according to the present invention received therein and positioned within the mouth of a subject for delivery of a powder dose;

FIG. 14 is a graph illustrating an amount of powder dose remaining after discharge of the powder dispenser of FIG. 1, as described in detail in experiment 1; and FIG. 15 is a graph illustrating an amount of powder dose remaining after discharge of the powder dispenser of FIG. 1 through an 18 inch tube, as described in detail in experiment 2.

DETAILED DESCRIPTION OF THE PREFERRED EMBODIMENT

Referring now to the drawings in detail, wherein like reference numerals indicate like elements throughout the several views, there is shown in FIG. 1 an elevational view of a powder dispenser 10 according to a preferred embodiment of the present invention. As is best illustrated in the sectional perspective view of FIG. 2 and exploded perspective sectional view of FIG. 3, the main components of the powder dispenser 10 include a means for regulating an introduction of a gas into the powder dispenser 10 comprising a guide member 12, a means for receiving a powder dose defining a chamber 14, a valve assembly 16 and a means for dispensing a powder dose from the powder dispenser 10 comprising a first fitting 18, a second fitting 20 and a generally elongated tube member 22. The structure of the components of the powder dispenser 10 are more fully defined below. For reason of clarity, FIGS. 2–5 have been enlarged 3×'s from that shown in FIG. 1.

The guide member 12, as best illustrated in FIGS. 2 and 3, comprises a generally elongated member and has a cavity 13 formed within a first end thereof which defines an inner surface, and the inner surface extends substantially through the guide member 12 and terminates by an end wall defining an air guide at its second end. The end wall of the guide member 12 is substantially a protrusion which extends generally outwardly from the second end thereof. The end wall includes at least one aperture extending therethrough and in a position proximate its peripheral surface, the purpose of which will be described below. In the present embodiment, as illustrated in FIG. 5, a plurality of apertures are shown which are at spaced intervals and extend completely around the perimeter thereof. As shown in FIGS. 2 and 3, the guide member 12 also includes provided within its outer surface and proximate its second end a series of threads for connection with the valve assembly 16.

As best illustrated in FIGS. 2 and 3, the valve assembly 16 comprises a generally elongated tube member and a valve means 21. The tube member includes an inner surface having a threaded section therein proximate a first end for receiving the guide member 12 for mounting. The inner surface is also provided with a threaded section proximate its second end which receives the first fitting 18, as will be set forth in more detail below. In addition, the portion of the inner surface of the valve assembly 16 extending between the two threaded ends is generally planar relative to its outer surface. As illustrated, the diameter of the generally planar inner surface that extends between the threaded ends is generally less than the diameter of the threaded end sections. Further, the threaded section of the first end and the generally planar section of the inner surface are connected by a substantially tapered surface 23.

The valve means 21 of the valve assembly 16 is best illustrated in FIGS. 4*a* and 4*b*. As illustrated the valve means 21 is comprised of two separate members in the present embodiment. These portions include a generally elongated first body member 24 and a second generally elongated body member 26. The first body member 24 is defined by first and second ends and includes an outer surface and an inner surface. The inner surface of the first body member 24 is substantially tapered proximate its first end inwardly towards the direction of the second end. In addition, the outer surface of the first body member 24 proximate to the first end includes a flange surface 27. Further, a "bill" comprising a pair of substantially parallel lips 25 are provided extending from the second end of the first body member 24. The lips 25 include outer and inner surfaces with a passage provided between the inner surfaces of the lips 25. In addition, the passage extending between the lips 25 is also provided through the second end of the first body member 24 and terminates within the tapered inner surface thereof. The second body member 26 is also defined by first and second ends and similarly includes a substantially tapered inner surface and flange surface 29 as in the first body member 24. Further, a passage is also provided within the second body member 26 through its second end and terminates within the inner surface thereof. In the present embodiment, as illustrated in FIG. 4a, a very short pair of lips is seen extending from the second end of the second body member 26. However, it should be noted that the short length of lips extending from the second body member 26 are not required and can be eliminated so that the second end is planar along the length thereof. In one example, the first and second body members 24 and 26 can comprise two conventional "duckbill valves" of appropriate size, such as one type manufactured by Vernay Laboratories, Inc., Model No. VA3426. In this example, the "bill" of the second valve would be removed in accordance with the second body member 26.

Figure 3:
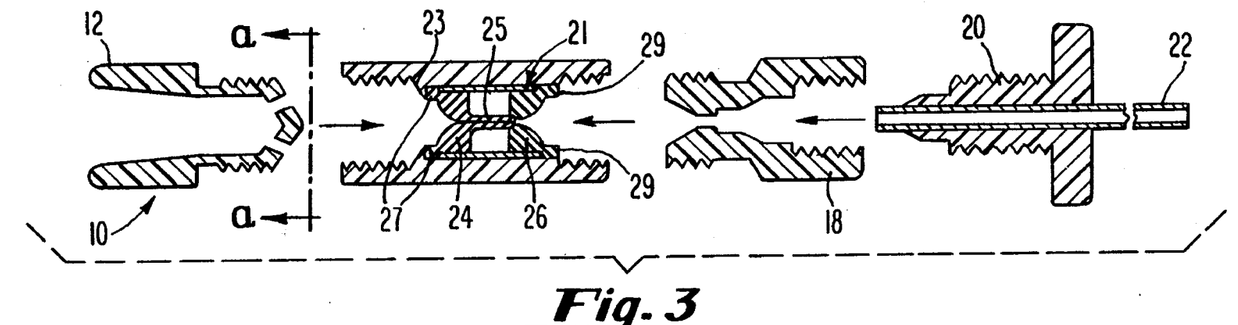
Figure 4B:
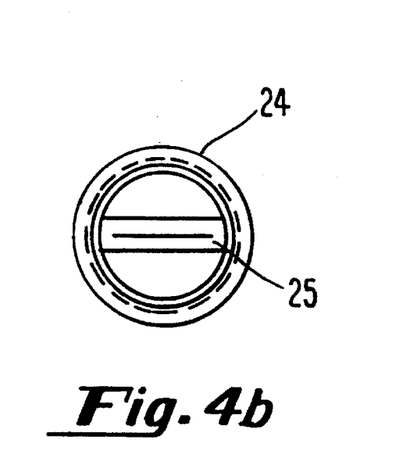

For assembly of the valve means 21, shown in FIG. 4 the lips 25 extending from the first body member 24 are inserted into the passage extending through the second body member 26 and terminate proximate the tapered inner surface thereof. Further a generally elongated cylindrical support member 28 is provided in which the first and second body members 24 and 26 are assembled. The support member 28 is included with a generally cylindrical inner surface which receives the body members 24 and 26 on assembly. The first body member 24 is inserted into one end of the support member 28 and the second body member 26 is inserted into the second end of the support member 28. When assembled, the flanges 27 and 29 of the body members 24 and 26 are positioned against the end surfaces of the support member 28 as shown in FIGS. 2–4.

As described above, in the present embodiment the valve means 21 is illustrated as comprising the two separate body members 24 and 26, however it should be understood that the valve means 21 can be provided as a single unitary piece. In particular, the lips 25 extending from the first body member 24 as shown in FIG. 4 would also extend out from the second end of the body member 26. As to the composition of the valve means 21, in the present embodiment this is comprised of an elastomeric material but it should be understood that any suitable compliant material could also be used for the same purpose. Furthermore, it should be understood that other types and configurations of valve means or similar valve devices can also be utilized without departing from the spirit of the present invention; the salient feature of the valve means being that a very low "cracking pressure" is required in order to open the valve to permit flow in the preferred direction.

Figure 2:
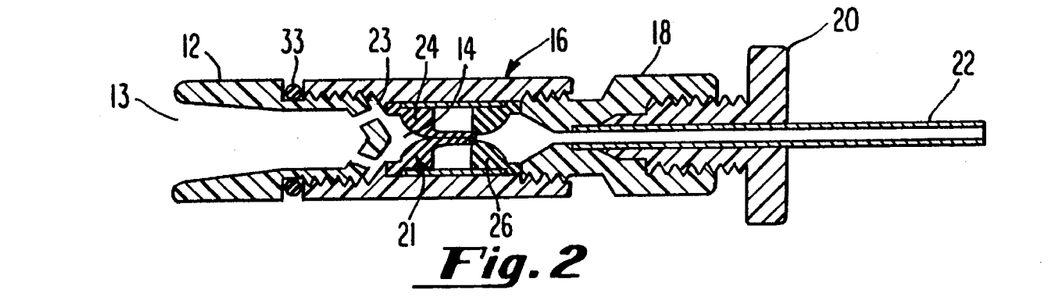

As illustrated in FIGS. 2 and 3, the first fitting 18 as shown is comprised of a generally elongated member and is included with a threaded section proximate a first end thereof which is configured to be received by the valve assembly 16 for connection. The inner surface of the first fitting 18 as shown is tapered generally inwardly at its first end. The remaining portion of the inner surface of the first fitting 18 is configured corresponding to the configuration of the outer surface of the second fitting 20. The first fitting 18 also includes a threaded section proximate a second end for receiving the second fitting 20, as will be described below.

The second fitting 20 is generally elongated and has a substantially cylindrical passage therethrough which receives the generally elongated tube member 22. The second fitting 20 includes an outer section which is received by the first fitting 18, which includes a substantially tapered section proximate a first end thereof through which the generally elongated tube member 22 passes. In the present embodiment, the second fitting 20 is comprised of a chromatography type fitting, preferably a 10-32 male nut manufactured from standard thermoplastic or thermosetting materials.

The generally elongated tube member 22 noted above comprises a generally elongated cylindrical tube member having a correspondingly configured channel extending therethrough. In the present embodiment the tube member 22 is comprised of stainless steel, however other suitable materials such as flexible plastic tubing could also be utilized for this purpose.

The assembly of the powder dispenser 10 will now be described in relation to FIGS. 2 and 3. After the valve means 21 has been inserted within the inner surface of the support member 28, the support member 28 is mounted within the inner surface extending between the two tapered ends of the valve assembly 16. The guide member 12 is received within the first end of the valve assembly 16 and coupled by the corresponding threaded areas. As illustrated in FIG. 2, the sample chamber 14 is formed between the inner surface of the first body member 24 of the valve means 21 and the protrusion of the guide member 12.

The chamber 14 is configured of a predetermined size and receives the powder dose which is to be dispensed from the powder dispenser 10. In accordance with the present invention, the size of the chamber 14 is adjustable in order to accommodate doses of varying quantities. For this purpose, a number of O-ring seals can be mounted around the second end of the guide member 12 and positioned against the flange which is provided along the outer surface. In the present embodiment, a single O-ring seal 33 is shown in FIG. 2, however it should be understood that any number of O-rings or other air-tight spacers can be provided in order to increase the size of the chamber 14.

The first fitting 18 is received within the second end of the valve assembly 16 and connected by the corresponding threaded areas. As illustrated in FIG. 2, when fully assembled the first end of the first fitting 18 is engaged with the flanges of the body member 26 of the valve means 21. The second fitting 20 is received within the second end of the first fitting 18 and engaged by the threaded end portions for connection of the two members. In this position, since the outer surface of the second fitting 20 is configured corresponding to the inner surface of the first fitting 18, there is no open space provided between these two members when mounted.

Figure 1:
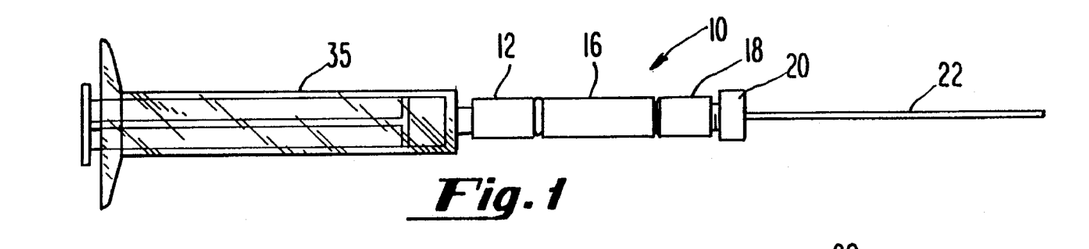

As to the composition of the guide member 12, valve assembly 16 and first fitting 18, in the present embodiment these portions are comprised of standard thermoplastic or thermosetting materials however it should be understood that any suitable material could be provided for this purpose. Furthermore, as illustrated in FIG. 1, preferably the guide member 12, valve assembly 16 and first fitting 18 are formed having a knurled outer surface which provides an improved gripping surface when the portions are rotated relative to one another for assembly or disassembly.

Figure 5:
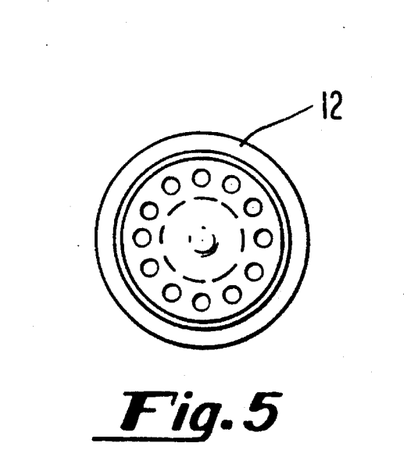

The operation of the powder dispenser 10 according to the present invention will now be described. The powder dispenser 10 is provided in connection with an actuating means which is adapted to deliver the powder dose provided in the chamber 14 for dispensing from the device 10. In the present embodiment, the actuating means comprises a conventional syringe 35 as is illustrated in FIG. 1. In accordance with the present invention, the actuating means is adapted to provide an amount of a gas which is introduced into the guide member 12 for delivering the powder dose. For this purpose, the syringe 35 operates as an actuating means by introducing air as the type of gas into the guide member 12. Other types of actuating means and gases can also be used for the same purpose without departing from the spirit of the present invention. For instance, the present invention can be adapted for use with an actuating means comprising other controllable, pulsatile air sources or containers of compressed gas. In the present embodiment, the syringe 35 is charged with air by pulling back on the syringe plunger and then secured to the powder dispenser 10 by the guide member 12. The cavity 13 of the guide member 12 as illustrated in the figures is configured to receive the tapered end of the syringe 35. Subsequent actuation of the syringe plunger to its closed position introduces the air from the syringe 35 into the guide member 12. The air which enters the guide member 12 passes through the apertures extending through the second end around the periphery thereof, as shown in FIG. 5. The arrangement of the apertures through the second end of the guide member 12 regulates the air passing therethrough and into the chamber 14. In particular, the incoming air is constrained to flow in the shape of a hollow cylinder, which operates to scavenge powder from both the inner surface of the valve assembly 16 and the valve means 21 within the valve assembly 16 in order to entirely empty the chamber 14 and prevent "coring" of the sample. A slight pressure buildup is required to overcome the resistance of the valve means 21, and the powder dose sample is driven through the valve means 21 and into the first fitting 18. Because of the slight pressure buildup, the powder dose exits the valve means 21 in a bolus or small "puff". As noted above, the valve means 21 operates to allow passage of the powder dose only when the syringe plunger is actuated to the closed position; otherwise, the powder dose sample is prevented from passing through the valve means 21. The powder dose entering through the first fitting 18 passes into the generally elongated tube member 22 secured within the second fitting 20. The powder dose from the generally elongated tube member 22 is dispensed from the powder dispenser 10. Furthermore, in the present embodiment, the powder dispenser 10 preferably is operated from a substantially vertical position in order to prevent possible passage of a portion of the powder dose sample from the chamber 14 back through the apertures formed in the guide member 12. Accordingly, when the powder dispenser 10 is in a substantially vertical position, the powder dose cannot pass through the apertures in the guide member 12 nor will it pass through the valve means 21 prior to actuation of the syringe 35.

As noted earlier, an important aspect of the present invention is that the powder dispenser 10 is configured of a "zero dead space" or "totally swept volume" design which facilitates the dispensing of the powder dose. In particular, as noted in FIG. 2, there are smoothly tapered or radiussed transitions between the various parts and no sharp edges or areas where small amounts of powder can avoid the air stream. Specifically, the transition between the guide member 12 to the cheer 14, from the cheer 14 to valve means 21 of the valve assembly 16, and from the valve means 21 to the first fitting 18 are substantially tapered and radiussed in configuration. Furthermore, the second fitting 20 is configured to be received within the first fitting 18 so that there are no spaces formed therebetween.

In addition, improved powder dispensing is also due to the operation of the valve means 21. In particular, the air when flowing through the valve operates to cause the lips 25 of the first generally elongated body member 24 to vibrate and oscillate relative to one another, which serves to further improve the powder flow characteristics by de-agglomerating the powder as it passes through the valve.

Further, the configuration of the apertures through the air guide 12 facilitates passage of the powder dose from the chamber 14.

In FIGS. 14 and 15 are illustrations of preliminary trial experiments which exemplify the efficiency of powder dispension of the present invention.

The following examples are offered by way of illustration, not by way of limitation.

Experiment 1

The powder dispenser tested was the same as that identified above and included a two-inch long, straight tube member comprised of 18-gauge stainless steel tubing.

The powder dose sample utilized was lactose and the amount of the sample varied in each trial. There were a total of six trials and the size of the powder dose was 2.7 mg. in trial 1, 3.1 mg in trial 2, 2.1 mg in trial 3, 2.2 mg in trial 4, 2.2 mg in trial 5, and 13.5 mg in trial 6.

In each trial the syringe was charged with 3 cc of air except for trial #5 where 1 cc was utilized.

The orientation of the powder dispenser was vertical.

For each trial, the percent of sample which remained in the device after actuation of the syringe was measured. This was accomplished by comparing the weights of the powder dispenser when empty (tare weight), when loaded with the powder dose sample (gross weight) and after the powder dose had been discharged (net weight).

Results

FIG. 14 illustrates the results of the first experiment. The graph shows that greater than 90% of the powder dose sample was delivered from the device after a single discharge. In particular, in trial 1 about 5% of the sample remained, trial 2 about 7%, trial 3 about 2.5%, trial 4 about 7.5%, trial 5 about 2% and trial 6 about 2.5 %.

In addition to the foregoing, another important aspect of the present invention, in particular, in relation to the efficiency of powder dispensing, is in the types of applications for using the device. In particular, the present invention can be adapted for delivery of a powder dose intratracheally, near the carina, which bypasses the potential for large losses of the powder dose to the mouth, throat, trachea, etc. In addition, in operation the gas passed from the actuating means will serve to slightly insufflate the lungs, which provides increased powder penetration. For the intratracheal insertion, the tube member 22 can be effected through an endotracheal tube in anesthetized, ventilated subjects, including animal or human patients, or in conscious subjects, the tube member 22 can be inserted directly into the trachea preferably using a small dose of local anesthetic to the throat and/or a small amount of anesthetic on the tip of the tube member 22, in order to minimize a "gag" response. In accordance with the present invention, the delivery tube member 22 can be provided of any length, or an additional tube member can be utilized which is attached to the delivery tube member 22. The additional tube member can be comprised of any material (i.e., plastic, stainless steel, etc.) and of any small diameter which is sufficiently sized for intratracheal insertion. Preliminary studies with delivery tubes up to 18 inches in length have shown that such tubes have no affect on the ability of the powder dispenser 10 to quantitatively deliver a powder dose; this is illustrated by the following example.

Experiment 2

Method and Materials

The present experiment was similar to the experiment noted above except that the powder dispenser was provided in connection with an 18-inch long small-diameter plastic tube. The plastic tube utilized was a Cordis angiographic catheter.

The powder dose sample utilized was again of lactose and varied for each trial. There were two trials conducted. In trial 1 the size of the sample was 5.25 mg and in trial 2 the sample size was 5.05 mg.

The syringe was set with 3 mm of air for each trial run.

Results

FIG. 15 is a graphic illustration of the second experiment. The graph shows that greater than 90% of the powder dose was delivered from the powder dispenser after a single discharge. In particular, in trial 1 about 7% of the powder dose remained in the dispenser after discharge and in trial 2 about 2.5% of the powder dose remained after discharge.

Furthermore, another aspect of the application of the powder dispenser of the present invention is that the device can also be adapted for use in general in vitro handling of dry powders in preparation for procedures such as microscopic examination or particle size analysis. In this type of application a shorter length of the tube member 22 would only be required.

Figure 6:
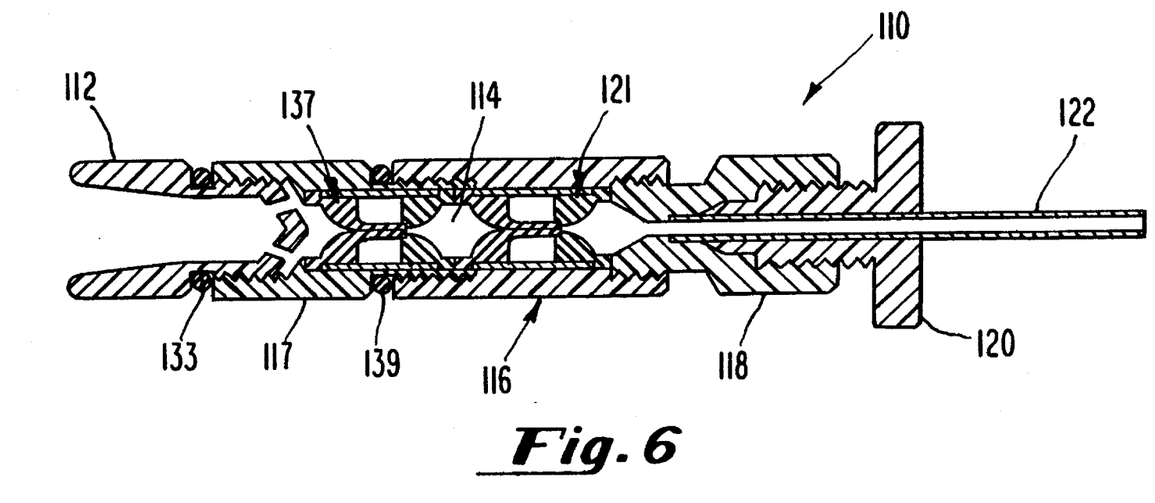
Figure 7:
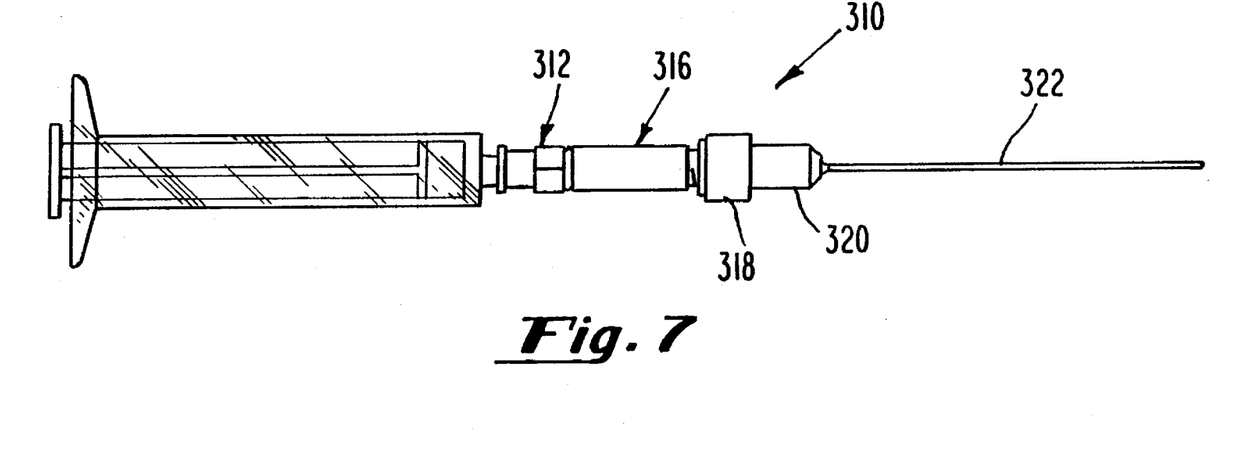

In FIG. 6 is illustrated a side sectional elevational view illustrating a second embodiment of the powder dispenser according to the present invention. The powder dispenser 110 as illustrated in FIG. 6 is identical to that illustrated in FIG. 1 except that the powder dispenser 110 includes an alternate valve assembly 116. In this embodiment, the portions in FIG. 6 which correspond to that identified in FIGS. 1 through 5 are identified by the same number designation except beginning with the number 100 for reason of clarity. Further, for simplicity, only those features which are different from the first embodiment will be described below.

In the second embodiment, as noted in FIG. 6, the valve assembly 116 includes as a portion thereof a second valve assembly 117. The valve assembly 117 is provided disposed between the first fitting 118 and guide member 112. Similar to, the valve assembly 16 in embodiment 1, the valve assembly 117 is a generally elongated member which includes an outer surface and an inner surface for receiving a second valve means 137. The inner surface of the valve assembly 117 is provided with a threaded area at a first end thereof for receiving the guide member 112. The outer surface of the valve assembly 117 is provided with a threaded section proximate its second end for engagement with the threaded inner surface of the first portion of the valve assembly 116 corresponding to the valve assembly 16 from embodiment 1. The inner surface of the valve assembly 117 also includes an area proximate its middle which is substantially planar for receiving the second valve means 137. On assembly, the end portions of the flanges of the first and second valve means 121 and 137 are in engagement with one another and form the chamber 114 therebetween as illustrated in FIG. 6. The valve assembly 117 can also be adapted to receive a number of O-ring seals or other air-tight spacers as noted below.

Figure 8:
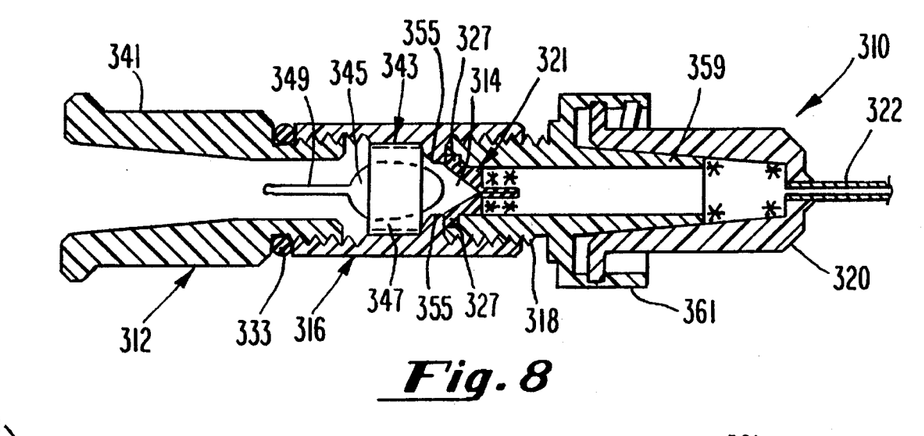
Figure 9:
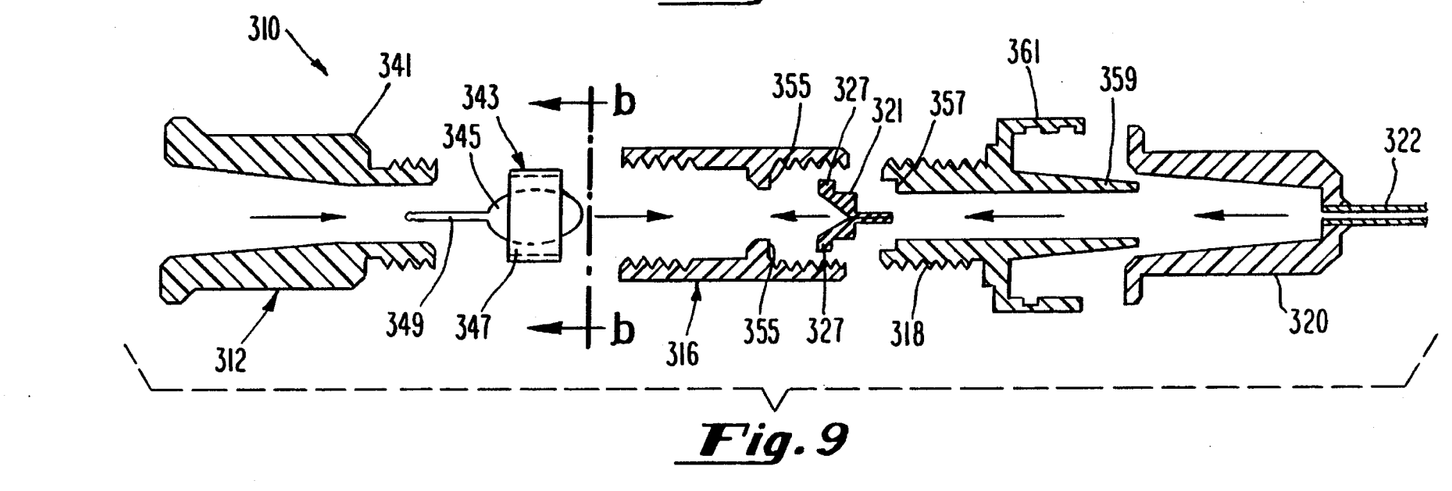

In operation of the powder dispenser 110 illustrated in FIG. 6, the powder dose is loaded within the chamber 114 provided between the two valve means 137 and 121. Similar to the first embodiment, the size of the chamber 114 can be adjusted by varying the number of O-ring seals or other air-tight spacers provided around the valve assembly 117; in the present embodiment a single O-ring seal 134 is shown. The remaining operation of the powder dispenser 110 corresponds to that of the powder dispenser 10 of the first embodiment of the present invention.

An important feature of the powder dispenser 110 is that the device can be used in any orientation (vertical, anti-vertical, horizontal, etc.) without sacrificing quantitative delivery of the powder dose. For example, as indicated earlier with respect to the first embodiment of the present invention, the powder dispenser 10 was indicated to operate best when in a vertical position due to the apertures extending through the guide member 12. However, in the present embodiment, the powder dose is confined within the chamber 114 between the first and second valve means 137 and 121 until operation of the actuating means.

FIGS. 7–10 illustrate a third embodiment of the present invention comprising a powder dispenser 310. In this embodiment, the portions which correspond to the earlier two embodiments will be indicated by the same number designations but beginning with the number 300. As best illustrated in FIGS. 8 and 9, the main components of the powder dispenser 310 include a guide member 312, a chamber 314, valve assembly 316, first fitting 318, a second fitting 320 and an generally elongated member 322. Similar to FIGS. 1–5, FIGS. 8–10 have been enlarged 3×'s from FIG. 7 for reason of clarity.

The guide member 312 is comprised of two components. As best shown in FIGS. 8–9, the first is a generally elongated tube member 341 which includes a generally cylindrical aperture extending therethrough and is provided with a threaded area proximate its first end along its outer surface. The second component of the guide member 312 is an air guide 343. The air guide 343 comprises as portions thereof a body 345 which defines a generally prolate ellispoidal member, a substantially annular split-ring member 347 in spaced separation from and uniformly surrounding the outer surface of the body member 345 and a substantially elongated carrying member 349 attached to one end of the body member 345. As best illustrated in FIG. 10, the split-ring member 347 is included with a cut-out 351 formed through its surface and is attached to a connecting member 353 for coupling the split-ring member 347 to the body member 345. The space between the body 345 and split-ring member 347 provides the aperture for allowing the passage of gas through the guide member 312. The substantially elongated carrying member 349 is a generally elongated cylindrical member and includes a substantially annular groove adjacent its distal end for facilitating removal and/or insertion by an operator of the device. In the present embodiment, the composition of the air guide 343 is of stainless steel, however other suitable materials can also be provided.

The valve assembly 316 as shown in FIGS. 8 and 9 comprises a generally elongated member having an inner surface which is provided with threaded areas on its end portions. Further, the inner surface of the valve assembly 316 between the threaded end portions includes a generally planar section which is terminated by a generally elongated flange 355 extending from the inner surface.

The valve assembly 316 also includes a valve means 321 which corresponds in configuration to the generally elongated first valve body member 24 recited in the first embodiment of the present invention, and for this reason will not be described in further detail herein.

The first fitting 318 in the present embodiment comprises a standard male "luer lock" type of tapered fitting which comprises a generally elongated member including as its portions a generally cylindrical aperture extending therethrough, a substantially annular seating member 357 formed in a first end thereof as shown in FIG. 9, and a threaded area proximate its first end. Furthermore, the second end of the first fitting 318 includes a substantial annular inner tube member 359 surrounded by a substantially annular outer tube member 361 at spaced separation forming a cavity therebetween. As illustrated in FIGS. 8 and 9, the inner surface of the outer tube member 361 includes a threaded area therein. Further, the inner tube member 359 includes an outer surface which is tapered generally inwardly adjacent its second end.

The second fitting 320 in the present embodiment comprises a standard female luer hub which includes an inner surface which is generally tapered in a direction proximate a second end thereof to its first end. The second fitting 320 also includes an outer surface having a substantially annular flange proximate its first end.

The generally elongated tube member 322 in the present embodiment is provided as part of the second fitting 320 extending from the second end thereof.

On assembly, the valve means 321 is provided between the first fitting 318 and the valve assembly 316 and is positioned within the annular seating member 357 of the first fitting 318, and the first fitting 318 is then brought into threaded engagement with the valve assembly 316. As illustrated in FIGS. 8 and 9, when fully assembled, the top surface of the flange 327 of the valve means 321 is secured in engagement with the flange 355 extending from the inner surface of the valve assembly 316.

The second component 343 of the guide member 312 is inserted into the first end of the valve assembly 316 and secured in position against the flange 355 extending from the inner surface of the valve assembly 316, which is the side opposite of the valve means 321. The split-ring member 347 operates as a spring to securely locate the body member 345 coaxially within the inner surface of the valve assembly 316. The chamber 314 is provided between the valve means 321 and the second component 343 of the guide member 312 as best illustrated in FIG. 8. The first component of the guide member 312 is brought into threaded engagement with the threaded area of the first end of the valve assembly 316. Similar to the first embodiment of the present invention, the present embodiment also includes means for adjusting the size of the chamber 314 by providing a number of O-ring seals 333 or other air-tight spacers onto the first component of the guide member 312. The second fitting 320 is secured into threaded engagement with the first fitting 318, by the flange of the second fitting 320 being received within the threaded inner portion of the outer annular tube member 361 of the first fitting 318. Further, in this configuration, the inner tube member 359 of the first fitting 318 is received within the inner surface of the second fitting 320.

Figure 10:
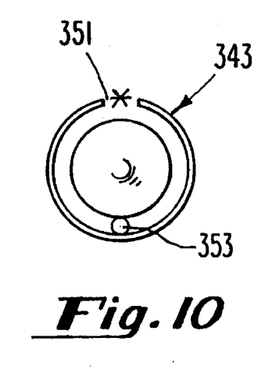

The operation of the powder dispenser 310 corresponds directly to that disclosed in relation to the first and second embodiments of the present invention. A difference resides in that the efficiency of powder dispension from the powder dispenser 310 is not as great as that in relation to the powder dispenser 10. Specifically, because of the configuration of the surfaces through the passage of the powder dispenser 310, areas of "dead space" are present within the powder dispenser 310 at the areas indicated by "*" in FIGS. 8 and 10, and for this reason the quantitative delivery of the powder dose of the present embodiment is not as great as that disclosed in relation to the first and second embodiments of the present invention.

An advantage of the powder dispenser 310 of the present embodiment is that some of the components (320, 312 and 318) can be fabricated by minor modification of commercially available fittings and thus provide for a quicker and less costly fabrication; the only portions which cannot be fabricated from commercially available parts are the second component 343 of the guide member 312 and the valve assembly 316. In particular, as noted above, the first component of the guide member 312 preferably comprises a standard female luer fitting, the first fitting 318 can comprise a standard male luer fitting, and the second fitting 320 a standard female luer hub. Further, the valve means 321 of the present invention can be comprised of a conventional "duckbill" valve, for example, a "duckbill valve" manufactured by Vernay Laboratories, Inc., Model No. VA3426 can be used for this purpose.

Figure 12A:
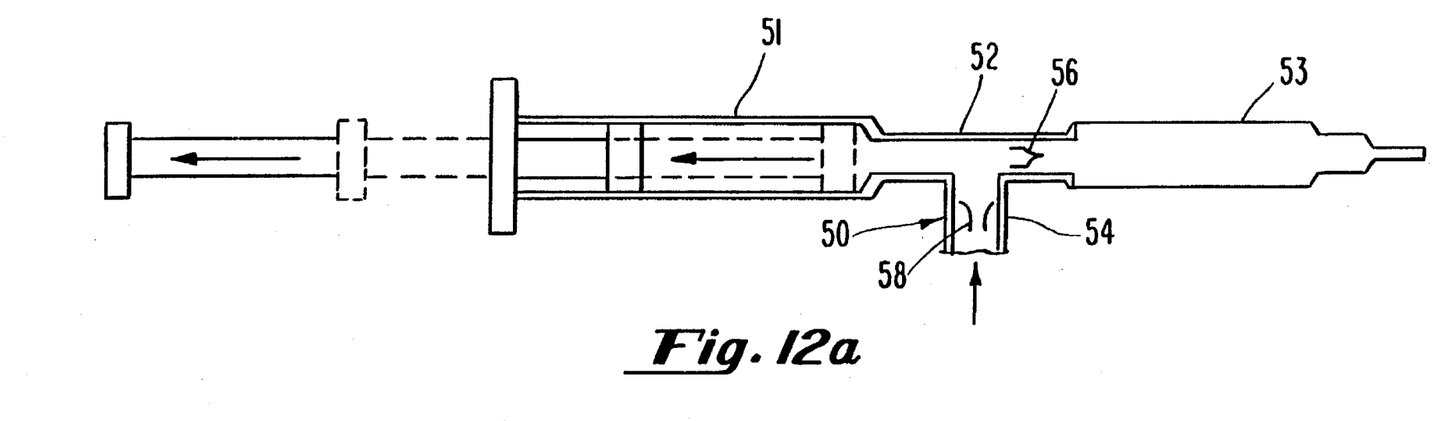
Figure 12B:
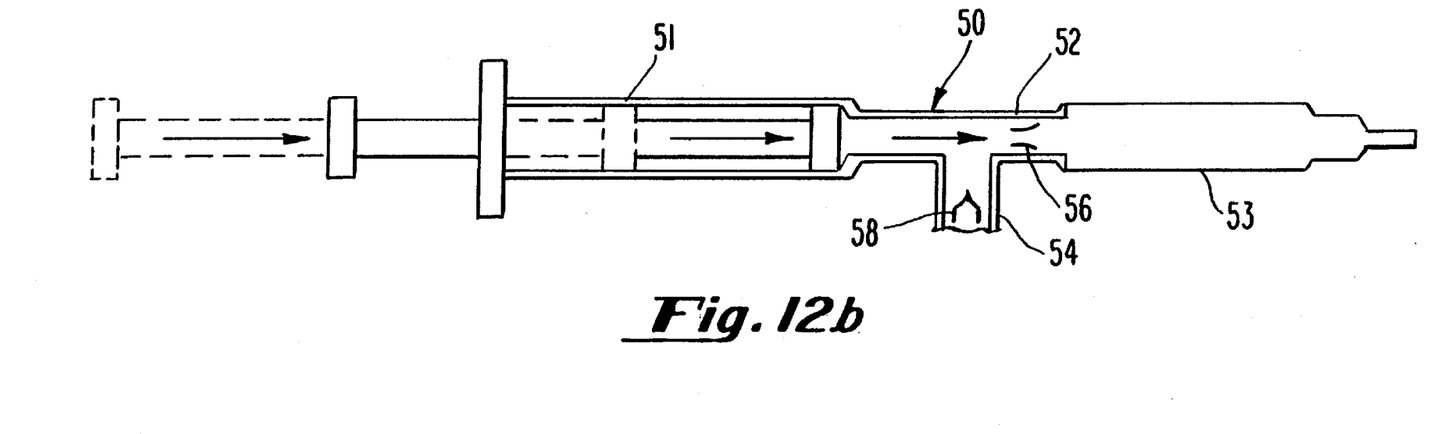

In FIG. 12 is illustrated an apparatus for charging the syringe when a syringe is used as the actuating means for the present invention. In particular, as noted earlier, the syringe plunger first has to be moved into the open position in order to charge the syringe with air prior to connection with the powder dispenser. Further, after the syringe is driven home into the closed position for actuating the device, the syringe then must be removed from the powder dispenser in order to again charge the syringe. The reason for this procedure is that the valve means of the present invention prevents the passage of matter in the direction opposite for delivery of the powder dose, in particular in this case air. In FIG. 12, the apparatus illustrated comprises a gas handling system 50 which allows charging of the syringe 51 without having to detach the syringe from the powder dispenser 53. The gas handling system 50 as shown comprises a generally T-shaped member including a first portion 52 defining a main body and a second portion 54 defining a side arm. The first portion 52 is adapted to be connected with the syringe 51 at a first end thereof and the powder dispenser 53 at a second end thereof. The T-shaped member also includes an inner surface which defines a passage extending through both the first and second portions 52 and 54 thereof. Further, the first portion 52 of the T-shaped member also includes a first valve means 56 positioned between the second portion 54 and the powder dispenser 53, and the second portion 54 of the T-shaped member includes a second valve means 58. The configuration of the first and second valve means 56 and 58 can comprise the valve means disclosed in either the first, second or third embodiments of the present invention or other similar valve devices. The important feature about the valve means of the gas handling system 50 is that the first valve means 56 be of a type which is open as the syringe 51 is discharged as is illustrated in FIG. 12b, and closed when the syringe plunger is retracted for charging, as illustrated in FIG. 12a. As to the operation of the second valve means 58, this must be adapted to be in a closed position as the syringe 51 is discharged when the plunger is driven home to the closed position, as is illustrated in FIG. 12b, and open when the syringe 51 is re-charged in FIG. 12a. In this manner, air will be allowed to flow through the second valve means 58 and into the syringe 51 as the syringe is charged, while during the same time period the first valve means 56 will remain closed in order to prevent possible passage of the powder dose therethrough. Furthermore, when the plunger is driven home for discharge of the syringe 51, the air will be allowed to pass from the syringe 51 and through the first valve means 56 for dispensing the powder dose, while during the same period the second valve means 58 will remain closed so that none of the air from the syringe 51 will be passed out to the atmosphere.

Figures 11, 13:
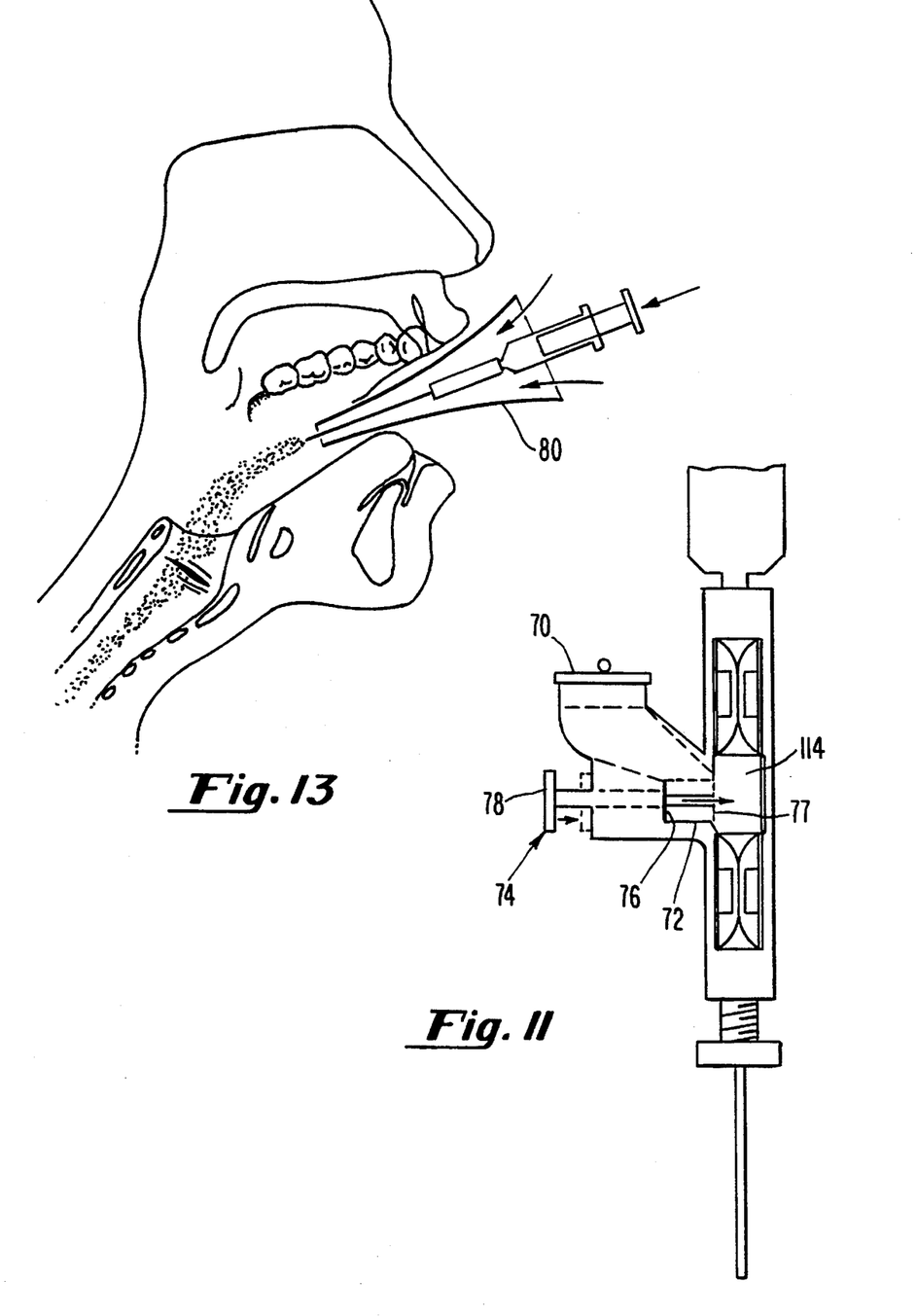

In FIG. 11 is illustrated an apparatus for loading of a powder dose into the powder dispenser without the need for opening and closing the guide member. In particular, as noted earlier in relation to the first, second and third embodiments of the present invention, the guide member is unscrewed from the valve assembly in order to allow loading of the powder dose in the chamber. The loading apparatus disclosed in FIG. 11 allows the powder dose to be inserted into the chamber without requiring the removal of the guide member. It is noted that in FIG. 11 the loading apparatus is illustrated in relation to the second embodiment of the present invention, however, it should be understood that this is for purposes of illustration only and the loading apparatus can also be applied to the remaining embodiments of the invention as well. The components of the loading apparatus illustrated in FIG. 11 includes a storage means or a container 70 for holding a bulk powder, a loading chamber 72 defining a passage extending from the container 70 to the chamber 114 of the powder dispenser and a latching means 74. In the present embodiment, the latching means 74 comprises a generally elongated member having a pair of substantially planar walls 76 and 77 at spaced separation which define the loading chamber 72 therebetween proximate a first end thereof and a button 78 at a second end. In the normally open position, the wall 77 defines part of the wall of the powder dispenser and thus seals the wall of the sample chamber 114. The generally elongated member is movable between an open position and a closed position. The latching means 74 further includes a biasing means comprising a cylindrical spring member for biasing the generally elongated driving member to its open position. The loading apparatus can be formed integral with the powder dispenser or as a separate member.

In operation of the loading apparatus illustrated in FIG. 11, the generally elongated driving member of the latching means 74 when in its open position allows the powder dose to pass from the container 70 to the loading chamber 72. The configuration of the loading chamber 72 is sized to receive an amount of bulk powder corresponding to the desired size of the powder dose. The button of the generally elongated driving member is then actuated by the operator which transfers the powder dose by the substantially planar portion 76 into the chamber of the powder dispenser. The generally elongated driving member is then returned to its open position by the biasing means.

FIG. 13 illustrates an aerodynamic guide adapted for housing the powder dispenser in accordance with the present invention for use as an inhalation device. The aerodynamic guide 80 as illustrated in FIG. 13 includes an outer surface and an opening therethrough defining a cavity, with the cavity being sufficiently large enough to receive the powder dispenser. In operation, as illustrated in FIG. 13, the aerodynamic guide 80 is placed into the mouth of a patient and the syringe is then actuated as the patient inhales for drawing the powder dose into the lungs. The cavity through the air guide provides a channel through which the patient's inhaled air is passed. In the present embodiment, the configuration of the aerodynamic guide 80 is generally conical, however other configurations could also be used.

Based on the foregoing, it should be understood that there are many advantages to the present invention. The present invention is designed to circumvent many of the problems in the pulmonary route of drug administration previously noted and is capable of quantitative delivery (greater than 90%) of a precisely-measured small dose of dry powder to the deep lung. This device features:

1) Its own air supply (e.g., air-filled syringe) which serves to slightly insufflate the lungs, thus increasing powder penetration. Preliminary studies of the pulmonary distribution of powdered dyes in rats using this device have found the dye to have penetrated to the farthest reaches of the lung accessible by manual dissection.

2) A small holding chamber which temporarily stores and positions the powder dose in preparation for the air charge, and 3) A delivery tube attached to the distal end of the device; this tube can be a small-diameter tube (such as 18-gauge needle tubing) and of any material (plastic, stainless steel, etc.), of any length. Preliminary studies with delivery tubes up to 18" in length have shown such tubes to have no effect on the ability of the device to quantitatively deliver small amounts of dry powder as illustrated in FIG. 15.

The dose is delivered intratracheally, near the carina, thus bypassing the potential for large losses to the mouth, throat and trachea, losses which greatly decrease the efficiency of dry powder inhalers. Intratracheal insertion of the delivery tube is effected through an endotracheal tube in anesthetized, ventilated patients or, in conscious patients, the delivery tube is inserted directly into the trachea using a small dose of local anesthetic to the throat and/or a small amount of anesthetic on the tube tip, in order to minimize the so-called "gag" response. This latter approach would be particularly applicable to emergency patients in acute bronchoconstriction, especially children and infants.

The protocol for quantitative use of this device is as follows:

1. The holding chamber is weighed (tare weight);
2. The chamber is opened and a small amount of powder is deposited within the chamber and the chamber is reclosed;
3. The chamber is re-weighed (gross weight);
4. The air supply syringe (or other controllable, pulsatile air source) is charged (syringe plunger is pulled back) and secured to the proximal end of the holding chamber;
5. The delivery tube is secured to the distal end of the holding chamber and the tube is inserted, either into an endotracheal tube or directly into the trachea, as described above.
6. The air pulse is delivered (e.g., the syringe plunger is pushed home), releasing the powder from the holding chamber and directing the powder through and out of the delivery tube;
7. The assembly is removed from the trachea or endotracheal tube, and the holding cheer is detached from the air supply and delivery tube;

8. The holding chamber is re-weighed (net weight).

There are several unique aspects of the design of the sample holding chamber which contribute to its effective performance in the protocol described above:

1. Prior to release by the air pulse, the powder sample is held securely in the holding chamber by a sensitive, "duckbill" type of one - way or "check" valve; this prevents loss of sample or contamination from the outside during handling and activation of the device.
2. The size of the sample chamber can be easily changed by varying the numbers of "O-ring" seals or other air-tight spacers.
3. A slight pressure build-up is required to overcome the valve resistance. For this reason, when the air charge is delivered, the powder dose exits the valve in a bolus or small "puff".
4. When the air pulse is delivered, air entering the holding chamber flows through a ring of small holes arrayed around the periphery of a smoothly-rounded projection which extends into the sample chamber cavity. The projection and ring of small holes together may be called an "air guide". The design described can be an integral air guide, or the air guide can also take the form of a removable part which performs the same function. Because of the air guide, incoming air is constrained to flow in the shape of a hollow cylinder, scavenging powder from the inner walls of the chamber and valve, and preventing "coring" of the sample; the entire chamber is swept clean.
5. The entire device is of the "zero dead space" or "totally swept volume" design, so that there are smoothly tapered or radiussed transitions between the various parts and there are no sharp edges or small dead spaces where small amounts of powder can avoid the airstream.

One aspect of the "zero dead space" design concerns the valve design, in which a typical "duckbill" valve is replaced with a novel valve configuration. In a standard "duckbill" valve installation in a tube, there is a small dead space behind the "bill" of the valve where powder emanating from the front of the "bill" can blow back and accumulate, for example, as indicated in FIG. 8; by constraining the front tip of the "bill" within a small cavity which is identical in size and shape to the "bill" and made of the same material so as to be compliant when the valve is activated, this problem can be avoided, since the dead space behind the "bill" has been eliminated. This is conveniently accomplished by removing the "bill" of one valve where it joins the valve body and inserting the "bill" of a second valve into the opening thus formed. When properly assembled and held in place in the present device, powder entering this valve assembly flows smoothly into the radiussed approach to the valve "bill", passes through the "bill", and exits into a similarly radiussed opening at the distal end of the holding chamber. In this way, the powder encounters only smooth transitions as it passes through the valve. This valve assembly can also be injection molded as a single piece.

Furthermore, when properly assembled, air flowing through this valve system will cause the emission of a high-pitched whistle, due to the vibration of the two parts of the valve "bill". This effect serves to further improve the powder flow characteristics by de-agglomerating the powder as it passes through the valve. In addition to its use for the in vivo administration of powdered drugs, described above, this powder conditioning effect makes this device useful for general in vitro handling of dry powders in preparation for analysis such as microscopic examination or particle size analysis.

Another aspect of the "zero dead space" design involves the use of "zero dead space" chromatography-type fittings for attachment of the delivery tube, as opposed to luer-type fittings which have a small inherent dead space, for example, as shown in FIG. 8.

The following variations on the basic design of this device serve to further broaden the scope of its application:

1. If a simple syringe is used to provide the air charge, a 3-way valving system can be interposed between the syringe and the holding chamber, as described in relation to FIG. 12. In this way, the syringe can be re-charged with air drawn from the outside without the inconvenience of removing the syringe from the sample holding chamber each time.
2. In general, this device performs best when used in the vertical position (pointing down). However, if, in addition to the valve assembly described above, which is located in the distal end of the holding chamber, a second such assembly is installed in the proximal end of the chamber, the device can be used in any orientation whatever (vertical, anti-vertical, horizontal, etc.) without sacrificing quantitative delivery of the powder dose such as described in relation to the second embodiment of the present invention.
3. Where only semi-quantitative performance is required, and a "zero dead space" type of device is not necessary, a simple device can be easily fabricated using only a single, standard "duckbill" valve and luer-type fittings, which have a small, inherent dead space, as described in the third embodiment of the present invention.
4. Although, in general, the use protocol described above provides for highly quantitative, reproducible delivery of small amount of drypowder, in practice the process of unsealing, loading, and re-sealing the sample chamber can be tedious. For this reason, the delivery device can be coupled to an ancillary device which allows for the transfer of small volumes of dry powder from a small hopper directly into the sample chamber of the delivery device, as is described in relation to FIG. 11. This can be done in such a way so as not to interfere with the flow of the air charge through the delivery device and consequent delivery of the powder dose. Such an ancillary storage/metering attachment could be made either integral with, or detachable from the main powder delivery device.
5. To improve penetration of powder into the lung, the air supply can be coupled to an appropriate valving system so as to introduce a small bolus of air into the lungs just prior to delivery of the powder dose. This air bolus will serve to slightly insufflate the lungs so as to make available a greater volume of free space in the lung passages, thus facilitating penetration of the delivered powder.
6. While the main thrust of this description has been directed towards the use of this device as part of an intratracheal delivery system for dry powders, this assembly could also be integrated into a system using an inhaler to draw the powder into the lungs as the delivery device is being activated from an essentially intra-oral position, as described in relation to FIG. 13. This type of configuration, in which the delivery device provides a source of energy for powder dispersion in addition to that provided by the patient's inhalation, has been shown to greatly improve the efficiency of dry powder delivery in other systems.

It will be recognized by those skilled in the art that changes may be made by the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

I claim:

1. A method for dispensing an amount of a powder dose from a powder dispenser wherein substantially the entire powder dose is dispensed from said powder dispenser, said method comprising the steps of:

providing a dispenser assembly, said dispenser assembly being adapted for connection with an actuating means for dispensing said powder dose, said dispenser assembly including means for receiving said powder dose, means for dispensing said powder dose connected with said receiving means, and a passage through at least a portion of said receiving means and said dispensing means for delivery of said powder dose, said passage through said receiving means defining an inner receiving means surface and said passage through said dispensing means defining an inner dispensing means surface, wherein said inner receiving means surface at least adjacent its connection with said dispensing means is substantially tapered outwardly in a direction of said dispensing means, and said inner dispensing means surface at least adjacent its connection with said receiving means is substantially tapered outwardly in a direction of said receiving means, whereby said passage is configured for delivery of substantially the entire amount of said powder dose;

providing said powder dose in said dispenser assembly;

providing said dispenser assembly in communication with said actuating means; and actuating said actuating means for dispensing substantially the entire amount of said powder dose from said powder dispenser.

2. A method according to claim 1 further including the step of providing said passage configured for dispensing at least about 90% of said powder dose from the powder dispenser.

3. A method according to claim 1 further including the step of providing said passage configured with minimal dead space therethrough.

4. A method according to claim 3 further including the step of providing said passage configured with substantially tapered and radiussed surfaces for providing minimal dead space therein.

5. A method according to claim 1 further including the step of de-agglomerating said powder dose as said powder dose is delivered through said passage.

6. A method according to claim 5 further including the step of providing valve means having at least one pair of substantially parallel valve lips, said valve lips oscillating as said powder dose passes through said valve lips for de-agglomerating said powder dose.

7. A method according to claim 1 further including a step of providing a valve means comprising a generally elongated body member defining first and second ends, with said second end of said body member being in engagement with said dispensing means, said valve means having an inner surface for passage of said powder dose to said passage through said dispensing means, said inner surface of said body member of said valve means proximate said second end thereof being configured substantially tapered outwardly in the direction of said dispensing means.

8. A method according to claim 7 further including the step of providing said inner surface of said body member proximate said first end thereof configured substantially tapered outwardly in the direction opposite of said dispensing means.

9. A method according to claim 1 further including the step of providing said dispensing means including a first fitting and a second fitting having a first end connected to said first fitting, said first fitting including an inner surface for delivering said powder dose to said second fitting and said second fitting including an outer surface for connecting with said first fitting, said first fitting defining first and second ends, with said second end of said first fitting being connected to said second fitting and said inner surface of said first fitting proximate said second and thereof being configured corresponding to said outer surface of said second fitting at least proximate said first end of said second fitting, whereby at least a portion of said outer surface of said second fitting is in flush engagement with said inner surface of said first fitting at least proximate said second end of said first fitting.

10. A method according to claim 9 further including the step of providing a delivery tube in said dispensing means, with said second fitting including an inner surface receiving said delivery tube, whereby said delivery tube defines an opening therethrough for receiving the powder dose delivered from said first fitting, wherein said inner surface of said first fitting proximate said second end thereof further defines a substantially annular seat for receiving a first end of said delivery tube, wherein said opening through said delivery tube at least at the first end thereof is of a predetermined diameter, and said inner surface of said first fitting proximate said first and thereof at least adjacent said first end of said delivery tube defines a passage of a diameter equal in size to the predetermined diameter of the delivery tube.

11. A method according to claim 10 further including the step of providing a chromatography fitting as said second fitting.

12. A method according to claim 1 further including the step of providing delivery means for pulmonary delivery of said dispensed powder dose to a subject;

providing at least a part of said delivery means at least into the mouth of said subject; and actuating said actuating means for dispensing said powder dose.

13. A method according to claim 12 further including the step of providing an amount of a gas into the lungs of said subject just prior to pulmonary delivery of said powder dose.

14. A method according to claim 12 further including the step of providing said delivery means intratracheally in said subject either directly or through a previously inserted endotracheal tube.

* * * * *